United States Patent [19]

Cugola et al.

[11] Patent Number: 5,510,367
[45] Date of Patent: Apr. 23, 1996

[54] INDOLE DERIVATIVES

[75] Inventors: Alfredo Cugola; Giovanni Gaviraghi, both of Verona, Italy

[73] Assignee: Glaxo SpA, Italy

[21] Appl. No.: 351,762

[22] Filed: Dec. 8, 1994

Related U.S. Application Data

[63] Continuation of Ser. No. 046,947, Apr. 15, 1993, Pat. No. 5,373,018.

[30] Foreign Application Priority Data

Apr. 16, 1992 [GB] United Kingdom ............... 9208492

[51] Int. Cl.$^6$ ..................................... A61K 31/405
[52] U.S. Cl. ............................................. 514/419
[58] Field of Search ............................... 514/419

[56] References Cited

U.S. PATENT DOCUMENTS

| | | | |
|---|---|---|---|
| 3,010,971 | 11/1961 | Kaier et al. | 260/319 |
| 4,960,786 | 10/1990 | Salituro et al. | 514/419 |
| 5,043,334 | 8/1991 | Bell et al. | 514/207 |
| 5,145,845 | 9/1992 | Johnson et al. | 514/80 |
| 5,284,862 | 2/1994 | Bigge et al. | 514/419 |

FOREIGN PATENT DOCUMENTS

| | | |
|---|---|---|
| 0396124 | 11/1990 | European Pat. Off. |
| WO92/01670 | 2/1992 | WIPO. |
| WO92/16205 | 10/1992 | WIPO. |

OTHER PUBLICATIONS

Salituro et al., J. Med. Chem., 1992, 35, 1791–1799.

Rowley et al., Bioorganic & Medicinal Chemistry Letters, 1992, 2(12), 1627–1630.

Salituro et al., J. Med. Chem., 1990, 33, 2946–2948.

Gray et al., J. Med. Chem., 1991, 34, 1283–1292.

*Primary Examiner*—David B. Springer
*Attorney, Agent, or Firm*—Bacon & Thomas

[57] ABSTRACT

The invention relates to the compound of formula (I)

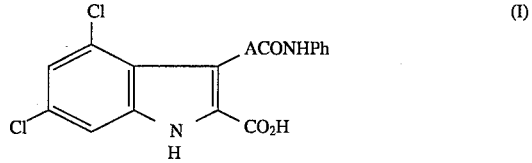

wherein A represents an unsubstituted ethenyl group in the trans (E) configuration or a physiologically acceptable salt or metabilically labile ester thereof which are antagonists of excitatory amino acids, to processes for their preparation and to their use in medicine.

7 Claims, No Drawings

INDOLE DERIVATIVES

This application is a continuation of U.S. Ser. No. 046,947, now U.S. Pat. No. 5,373,018, filed Apr. 15, 1993.

This invention relates to novel indole derivatives to processes for their preparation, to pharmaceutical compositions containing them and to their use in medicine. In particular it relates to indole derivatives which are potent and specific antagonists of excitatory amino acids.

U.S. Pat. No. 4,960,786 discloses that certain known 2-carboxylic indole derivatives are antagonists of excitatory amino acids. EP-A 0396124 also teaches that certain 2-carboxylic indole derivatives as being therapeutically effective in the treatment of CNS disorders resulting from neurotoxic damage or neurodegenerative diseases.

We have now found a novel 2-carboxyindole derivative that has a highly potent and specific antagonist activity at the strychnine insensitive glycine binding site located on the NMDA receptor complex.

Accordingly the present invention provides a compound of formula (I)

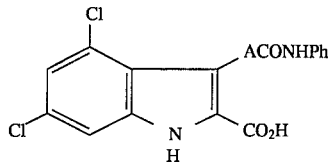

wherein A represents an unsubstituted ethenyl group in the trans (E) configuration, or a salt or metabolically labile ester thereof.

For use in medicine the salts of the compound of formula (I) will be physiologically acceptable thereof. Other salts however may be useful in the preparation of the compound of formula (I) or physiologically acceptable salts thereof. Therefore unless otherwise stated references to salts includes both physiologically acceptable base addition salts and non-physiologically acceptable base addition salts of compounds of formula (I).

Suitable physiologically acceptable base addition salts of compounds of formula (I) include alkali metal or alkaline metal salts such as sodium, potassium,, calcium, and magnesium, and ammonium salts formed with amino acids (e.g. lysine and arginine) and organic bases (e.g. procaine, phenylbenzylamine, ethanolamine, diethanolamine and N-methyl glucosamine).

It will be appreciated that the compound of formula (I) may be produced in vivo by metabolism of a suitable prodrug. Such prodrugs may be for example physiologically acceptable metabolically labile esters of compounds of the general formula (I). These may be formed by esterification, for example of any of the carboxylic acid groups in the parent compound of general formula (I) with where appropriate prior protection of any other reactive groups present in the molecule followed by deprotection if required. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters) or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-methoxy-1-methyl-ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1 -cyclohexyloxycarbonyloxyethyl, 1-(4-tetrahydropyranyloxycarbonyloxyethyl) or 1-(4-tetrahydropyranylcarbonyloxy)ethyl.

The compound of formula (I) and salts and metabolically labile esters thereof may from solvates e.g. hydrates and the invention includes such solvates.

Preferred salts of compounds of formula (I) include the potassium and more particularly the sodium salt thereof.

Preferred metabolically labile esters of compounds of formula (I) include $C_{1-4}$alkyl esters more particular methyl or ethyl, aminoalkyl esters more particular 2-(4'-morpholino)ethyl, or acyloxyalkyl esters e.g. acetoxymethyl pivaloxymethyl, 1-cyclohexyloxycarbonyloxyethyl or 1-(4tetrahydropyranyloxycarbonyloxy) ethyl.

The compound of formula (I) and or physiologically acceptable salts thereof are excitatory amino acid antagonists. More particularly they are potent antagonists at the strychnine insensitive glycine binding site associated with the NMDA receptor complex. As such they are potent antagonists of the NMDA receptor complex. Moreover the compounds of the invention exhibit an advantageous profile of activity including good bioavailibility and duration of action. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are useful in the treatment of chronic neurodegenerative diseases such as; Huntingdon's disease, Alzheimer's senile dementia, amyotrophic lateral sclerosis, Glutaric Acidaemia type, multi-infarct dementia, status epilecticus, contusive injuries (e.g. spinal cord injury), viral infection induced neurodengeration, (e.g. AIDS, encephalopaties), Down syndrome, epilepsy, schizophrenia, depression, anxiety, pain, neurogenic bladder, irritative bladder disturbances, drug dependency, including withdrawal symptoms from alcohol, cocaine, opiates, nicotine, benzodiazepine.

The potent and selective action of the compound of the invention at the strychnine-insensitive glycine binding site present on the NMDA receptor complex may be readily determined using conventional test procedures. Thus the ability to bind at the strychnine insensitive glycine binding site was determined using the procedure of Kishimoto. H et el. J Neurochem 1981, 37 1015–1024. The selectivity of the action of the compound of the invention for the strychnine insensitive glycine site was confirmed in studies at other ionotropic known excitetory amino acid receptors. Thus the compound of the invention was found to show little or no affinity for the kainic acid (kainate) receptor, α-amino-3-hydroxy-5-methyl-4-isoxazole-prop pionic acid (AMPA) receptor or at the NMDA binding site.

Compounds of the invention have also been found to inhibit NMDA induced convulsions in mice using the procedure Chiamulera C et el. Psychopharmacology (1990) 102, 551–552.

The neuroprotective activity of compounds of the invention has also been demonstrated in the middle cerebral artery occulsion preparation in mice, using the procedure described by Chiamulera C et el. European Journal of Pharmacology 216 (1992) 335–336. The compound was active when administered either pre-ischemia or post ischemia.

The invention therefore provides for the use of a compound of formula (I) and or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically labile ester thereof for the manufacture of a medicament for antagonising the effects of excitatory amino acids upon the NMDA receptor complex.

According to a further aspect the invention also provides for a method for antagonising the effects of excitatory amino acids upon the NMDA receptor complex, comprising administering to a patient in need thereof an antagonistic amount of a compound of formula (I) and/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 20–100mg preferably 60–80mg per day. For oral administration a daily dose will typically be within the range 200–800mg e.g. 400–600mg per day.

The desired dose may conveniently be presented in a single dose or as, divided doses administered at appropriate intervals, for example as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt or metabilcially labile ester thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation implant, rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters. propylene glycol or ethyl alcohol; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, tirchlorofluoromethane, dichloro-tetrafluoroethane, carbon dioxide or other suitable propellant, such as dichlorodifluoromethane, trichlorofluoromethane, dichloro-tetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in for example capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramusculady) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

The compound of formula (I) and salts or metabolically labile esters thereof may be prepared by reaction of the indole (II) in which $R_1$ is a carboxyl protecting group.

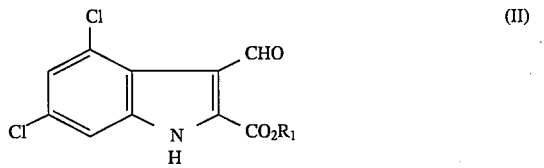

with a phosphorus ylide capable of converting the group CHO into the group ACONHPh, followed were necessary or desired by one or more of the following operations.

(1) removal of the carboxyl protecting group.

(2) Conversion of a compound in which $R_1$ is hydrogen atom or a carboxyl protecting group into a salt, or metabolically labile ester thereof.

Suitable carboxyl protecting groups $R_4$ include allyl, alkyl, trichloroalkyl, trialkylsilylalkyl or arymethyl groups such as benzyl, nitrobenzyl or trityl.

In one embodiment of this process the reaction may be carried using a phosphorus ylide of formula (111)

$(R_2)_3P=CH\ CONHPh$ (III)

wherein $R_2$ is an alkyl or phenyl group.

The reaction is carried out in aprotic solvent such as acetonitrile or an ether such as 1,4-dioxane and preferably with heating e.g. 40°–120°.

The carboxyl protecting group $R_1$ may be removed by conventional procedures known for removing such groups. Thus the group $R_1$ may be removed by hydrolysis using an alkali metal hydroxide e.g. lithium hydroxide in a solvent such as ethanol, followed where desired or necessary by that addition of a suitable acid e.g. hydrochloric acid to give the corresponding free carboxylic acid.

Physiologically acceptable salts of compounds of formula (I) may be prepared by treating the acid with the appropriate base e.g. alkali or alkaline earth metal hydroxide in an appropriate solvent such as an alkanol e.g. methanol.

Metabolically labile esters of compounds of formula (I) may be prepared by esterification of the carboxylic acid group or a salt thereof or by trans esterfication using conventional procedures. Thus for example acyloxyalkyl esters may be prepared by reacting the free carboxylic acid or a salt thereof with the appropriate acyloxyalkyl halide in a suitable solvent such as dimethylformamide. For the esterifcation of the free carboxyl group this reaction is preferably carried out in the presence of a quaternary ammonium halide such as tetrabutylammonium chloride or bewnzyltriethylammonium chloride.

Aminoalkyl esters may be prepared by transesterfication of a corresponding alkyl ester e.g. methyl or ethyl ester by reaction with the corresponding aminoalkanol at an elevated temperature e.g. 50°–150°.

Compounds of formula (II) may be prepared by treating the indole (IV)

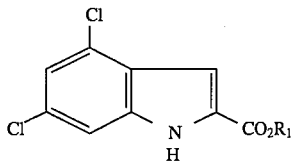
(IV)

wherein $R_1$ has the meansings defined above, with N-methylformanilide and phosphorous oxychloride in a solvent such as 1,2-dichloroethane.

The indoles of formula (IV) are either known compounds or may be prepared by analogus methods to these described for the known compounds.

In order that the invention may be more fully understood the following examples are given by way of illustration only.

In the Intermediates and Examples unless otherwise stated:

Melting points (m.p.) were determined on a Gallenkamp m.p. apparatus and are uncorrected. All temperature refer to C. Infrared spectra were mesured on a FT-IR instrument. Proton Magnetic Resonance ($^1$H-NMR) spetra were recorded at 300 MHz, chemical shifts are reported in ppm downfield (d) from $Me_4Si$, used as internal standard, and are assigned as singlets (s), doublets (d), doublets of doublets (dd), triplets (t), quartets (q) or multiplets (m). Colum chromathography was carried out over silica gel (Merck-AG Darmstaadt, Germany). The following abbreviations are used in text: EA=ethyl acetate, CH =cyclohexane, DCM= dichlormethane, DBU=1,8 diazabicyclo [5.4.0]undec-7-ene. DMF=N,N-dimethylformamide, MeOH—methanol. Tlc refers to thin layer chromatography on silica plates. Solution were dried over anhydrous sodium sulphate.

Intermediate 1

Ethyl 4,6-dichloroindole-2-carboxylate

To a solution of ethyl pyruvate (2.05 ml), in absolute ethanol (38 ml), concentrated sulphuric acid (0.5 ml) was added slowly under vigorous stirring. The resulting mixture was stirred at 23 for 10 minutes, then 3,5-dichlorophenylhydrazine hydrochloride (4 g) was added portionwise. The mixture was heated to reflux for 4 hours, cooled to 23°, poured into cold water (500 ml) and extracted with diethyl ether (3×300 ml). The organic layers were separated and dried. The solvent was evaporated under reduced pressure to give the 2-(3,5-dichlorophenylhydrazone)propionic acid ethyl ester as yellow solid (5 g; tlc DCM, Rf=0.79, 0.47) in E and Z isomers mixture. The solid was added to polyphosphoric acid (20 g) under stirring and the mixture was heated at 45° for 20 minutes to give a brown product which was crystallized by 95% ethanol (300 ml) to obtain the title compound as a yellow-brown solid (3.3 g;m.p.180°; Tlc DCM, Rf=0.54). IR($CDCl_3$) Vmax($cm^{-1}$)3440(NH), 1772-1709 (C=O). $^1$H-NMR($CDCl_3$) 9.00(s), 7.28(d), 4.42(q), 1.42(t).

Intermediate II

Ethyl 3-formyl-4.6-dichloroindole-2-carboxylate

A solution of N-methyl formanilide (5.19 g) and phosporous oxychloride (5.53 g) was stirred at 23° for 15 minutes. 1,2- Dichloroethane (60 ml) and intermediate I (6 g) were added and the resulting suspension was stirred at 80° for 6 hours. The reaction mixture was poured into a 50% aqueous solution of sodium acetate (300 ml) to give, by filtration, the title compound as a yellow solid (4.1 g; tlc EA/CH:⅘, Rf=0.4).

IR(Nujol) Vmax($cm^{-1}$) 1726 (C=O), 1663 (C=0), 1556 (C=C), 2725-2669 (CH). $^1$H-NMR(DMSO) 13.15(s), 10.60 (s), 7.54(d), 7.40(d), 4.43(q), 1.36 (t).

EXAMPLE 1

(E) Ethyl-3-[2 -(phenylcarbamoyl)ethenyl]-4,6-dichloroindole-2-carboxylate

DBU (319mg) was added to a stirred suspension of phenylcarbamoymethyl triphenylphosphoniumbromide (1 g) in acetonitrile (10 ml) at under nitrogen. Stirring was continued at 0⁰ for 15 minutes then intermediate II (680 mg) was added and the mixture refluxed for 6 hours. After dilution with dichloromethane (15 ml), the formed precipitate was collected by filtration giving the title compound (380 mg;tlc EA/CH:⅗, Rf=0.5) as a white solid.

IR(Nujol) Vmax($cm^{-1}$)3305-3288(NH), 1678-1662(C=O), 1627-1601 (C=C). $^1$H-NMR (DMSO) 12.61 (s),10.20 (s), 8.27(d), 7.73(d), 7.52(d), 7.36- 7.30(m), 7.06(m), 6.77(d), 4.39 (q), 1.36(t).

EXAMPLE 2

(E)3-[2-(phenylcarbamoyl)ethenyl]-4,6-dichloroindole-2-carboxylic acid

To a solution of Example 1 (250 mg) in ethanol (2.5 ml), lithium hydroxide (104mg) was added at 23°. The reaction was stirred at 50° for 6 hours then the solvent was evaporated and the residue dissolved in water (5 ml). The aqueous layer was acidified with 1N hydrochloric acid until a white solid precipitated. The latter was collected by filtration and dried to give the title compound as a white solid (230 mg).

IR(nujol) Vmax(cm$^{-1}$) 3402-3281-3192 (OH,NH), 1661(C=O),1607-1579 (C=C). $^1$H-NMR (DMSO) 12.4 (s), 10.1(s), 8.50(d), 7.74(d), 7.48(s), 7.27(t), 7.16(s), 7.11 (d), 6.99(t).

EXAMPLE 3

(E) 3-[2-(phenylcarbamoyl)ethenyl]-4,6-dichloroindole-2-carboxylic acid sodium salt Methanol was added dropwise to a suspension of (E)3-[2-(phenylcarbamoyl)ethenyl]-4,6-dichloroindole-2-carboxylic acid 200mg in 0.5M soldium hydroxide (1.01 ml) until a clear solution was obtained. After 15 minutes of stirring, the solution was evaporated to dryness and the residue was dried at 50° for 12 hours to give the title compound as a white solid (150 mg).

IR(nujol) Vmax(cm$^{-1}$) 3404-3126-(NH), 1624(C=O), 1600 (C=C). $^1$H-NMR (DMSO) 11.9(s), 10.06(s), 8.59(d), 7.75(d), 7.44(d), 7.27(t), 7.21(d), 7.10(d), 6.98(t).

EXAMPLE 4

(E)-2-[-2-(N,N-diethylamino)ethyl])3-[2-(phenylaminocarbonyl)ethenyl]-4,6-dichloroindole-2-carboxylate (E) Ethyl-3-[2-(phenyicarbamoyl)ethenyl]-4,6-dichloroindole-2 -carboxylate (0.3 g) and N,N-diethylethanolamine (1.3 g) were stirred for 20 minutes before sodium carbonate (0.078 g) was added and the mixture heated at 70° for 24 hrs. The solution was concentrated in vacuo and the residue left to stand overnight resulting in a white precipitate. Filtration and crystallisation from ethyl acetate yelded the title compound (0.13 g; Rf 0.65=DCM/MeOH:8.2) as a white solid.

IR(nujol) Vmax(cm$^{-1}$) 3300 (NH), 1676(C=O),1624 (C=C). $^1$H-NMR (DMSO) 12.52(s), 10.18(s), 8.22(d), 7.70(d), 7.50(d), 7.32(d), 7.31(t), 7.04(t), 6.73(d), 4.36(t), 2.75(t), 2.49(q), 0.90(t).

EXAMPLE 5

(E) 2-[4-(-2'N-morpholino)ethyl]3-[2-(phenylaminocarbonyl)ethenyl]-4,6-dichloroindole-2-carboxylate A mixture of (E) Ethyl-3-[2-(phenylcarbamoyl)ethenyl]-4,6-dichloroindole-2-carboxylate (400mg), 4-(2-hydroxyethyl)morpholine (7ml) and p-toluensulphonic acid (15 mg) was stirred at 130° for 120hrs. The mixture was, diluted with water and extracted with ethyl acetate (3×100 ml). The organic extracts were dried, concentrated and the precipitate collected to give the title compound as a white solid (110mg Rf 0.51=DCM/MeOH: 9/1, m.p=266°–267°).

$^1$H-NMR (DMSO) 10.21(s), 8.28(d), 7.75(d), 7.56-7.35(d,d), 7.35(t), 7.08(t), 6.74(d), 4.46(t), 3.54(m), 2.43(m), 2.70(t).

EXAMPLE 6

(a) (E)-2-(t-Butylcarbonyloxymethyl)3-[2-(phenylaminocarbonyl)ethenyl]-4,6-dichloroindole-2-carboxylate Example 2 (200mg) was dissolved in DMF (4 ml) and tetrabutylammonium chlodde (168 mg) was added. After stirring 0.5 h., chloromethylpivalate (118mg) was added dropwise and the reaction was stirred at room temperature for 48 hrs. The mixture was diluted with water and extracted with ethyl acetate (2×100 ml). The organic layer was washed with brine, dried and evaporated to give a crude product that was purified by flash chromatography to give the title compound as a yellow solid (190mg) m.p.=205°.

IR(nujol) Vmax(cm$^{-1}$). 3383-3308 (NH), 1747 (C=O), 1688 (C=O), 1634-1603(C=C).

$^1$H-NMR (DMSO) 12.75(s), 10.22(s), 8.22(d), 7.73(d), 7.54(d), 7.36(d), 7.33(t), 7.07(t), 6.79(d), 6.02(s), 1.15(s).

Using the same, general procedure the following compound were prepared:

(b) (E)-2-[1-(Tetrahydro-4-pyran-4-yloxycarbonyloxy)ethyl]3-[2-(phenylaminocarbonyl)ethenyl]4,6-dichloroindole-2-carboxylate From Example 2 (200 mg) in dry DMF (11 ml), benzyltriethylylammonium chloride (178mg) and 1 -(tetrahydro-4-H-pyran-4-yloxycarbonyloxy)ethyl chloride (244mg), after 4 days of stirring at room temperature the title compound was obtained as a yellow solid (209 mg). m.p.=209°.

IR(nujol) Vmax(cm$^{-1}$) 3300 (NH), 1749 (C=O), 1730 (C=O), $^1$H-NMR (DMSO) 12.73(s), 10.22(s), 8.21(d), 7.72(d), 7.53(d), 7.34(d), 7.32(t), 7.05(t), 6.901(q), 6.76(d), 4.76(m), 3.72(m), 1.87-1.53(m), 1.61(d).

(c) (E),2[1-(Cyclohexyloxycarbonyloxy)ethyl]3-[2-(phenylaminocarbonyl)ethenyl]-4,6-dichloroindole-2-carboxylate From Example 2 (300mg) in dry DMF (8 ml), benzyltriethylammonium chloride (178mg) and 1-(cyclohexyloxycarbonyloxy)ethyl chloride (242mg), after 0.5 hrs of stirring at room temperature, the title compound was obtained as a yellow solid (170 mg) m.p.=125°.

IR(nujol) Vmax(cm$^{-1}$) 3300 (NH), 1730 (C=O). $^1$H-NMR (DMSO) 12.71(sO, 10.21(s), 8.21(d), 7.71(d), 7.51(d), 7.36-7.26(m), 7.05(t), 6.85(q), 6.76(d), 4.54(m), 1.79(m), 1.51-1.1(m), 1.6(d).

(d) (E) -2[(Methoxycarbonylmethyl)3-[2-(phenylaminocarbonyl)ethenyl]-4,6-dichloroindole-2-carboxylate From Example 2 (200 mg) in dry DMF (4 ml), tetrabutylammonium chloride (168mg) and methyl chloroacetate (85mg), after 48 hrs of stirring at room temperature, the title compound was obtained as an off-white solid (210 mg). m.p.=241°–242°.

IR(nujol) Vmax(cm$^{-1}$) 3348(NH), 1749(C=O), 1672(C=O), 1634-1610(C=C). $^1$H-NMR (DMSO)12.8(s), 10.21(s), 8.28(d), 7.72(d), 7.54(d), 7.38-7.28(m), 7.06(t), 6.48(d). 5.02(s), 3.73(s).

Pharmacy Examples

| A. Capsules/Tablets | |
|---|---|
| Active ingredient | 200.0mg |
| Starch 1500 | 32.5mg |
| Microcrystalline Cellulose | 60.0mg |
| Croscarmellose Sodium | 6.0mg |
| Magnesium Stearate | 1.5mg |

The active ingredient is blended with the other excipients. The blend can be used to fill gelatine capsules or compressed to form tablets using appropriate punches. The tablets can be coated using conventional technqiues and coatings.

| B. Tablet | |
|---|---|
| Active ingredient | 200.0mg |
| Lactose | 100.0mg |
| Microcrystalline Cellulose | 28.5mg |
| Povidone | 25.0mg |
| Croscarmellose Sodium | 6.0mg |
| Magnesium Stearate | 1.5mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

| C. Injection Formulation | |
|---|---|
| Active ingredient | 0.1–7.00 mg/ml |
| Sodium phosphate | 1.0–50.00 mg/ml |
| NaOH qs desidered pH (range 3–10) | |
| water for injection qs to | 1 ml |

The formulation may be packed in glass (ampoules) with a rubber stopper (vials, syringes) and a plastic/metal overseal (vials only).

| D. Dry Powder for constitution with a suitable vehicle | |
|---|---|
| Active ingredient: | 0.1–100.00 mg |
| Mannitol qs to | 0.02–5.00 mg | packed in glass vials or syringes, with a rubber stopper and (vials only) a plastic metal overseal.

| E. Inhalation Cartridges | |
|---|---|
| | mg/cartridge |
| Active ingredient (micronised) | 5.00 |
| Lactose to | 25.00 |

The active ingredient is micronised in a fluid energy mill to a fine particle size range prior to blending with normal tabletting grade lactose in a high energy mixer. The powder blend is filled into a proper unit dose container as blister or capsule for use in a suitable inhalation or insufflation device.

The affinity of the compound of the invention for strychnine insensitvie glycine binding site was determined using the procedure of Kishimoto H. et al J. Neurochem 1981, 37,1015–1024. In this test the compound of Example 2 was found to have a pKi value of 8.5.

The ability of compounds of the invention to inhibit NMDA included convulsions in the mouse was determined using the procedure of Chiamulera C et al. Psychopharmacology 1990, 102, 551–552. In this test the ability of the compound to inhibit the generalized seizures induced by an intracerebroventricular injection of NMDA in mice was examined at a number of dose levels. From these results the dose required to protect 50% of the animals from the convulsive action of the NMDA was calculated. This expressed as mg/kg is referred to as the $ED_{50}$ value.

Representative results obtained for compounds of the invention when given by intravenous and oral administration are given in the following table.

| Ex No. | $ED_{50}$ iv | mg/kg po |
|---|---|---|
| 1 | 0.7 | 0.3–1 |
| 3 | 0.06 | 5.98 |
| 5 | 0.3 | 3.2 |
| 6 | 0.3 | 10 |

The compounds of the invention are essentially non toxic at therapeutically use ful doses. Thus for example the compound of Example 3 produced no untoward side effects when administered to rats and mice at doses of 3–30 mg/kg iv or 30-300 mg/kg orally.

We claim:

1. A method for the treatment or prevention of neurotoxic injury or neurodegenerative disease in a mammal including man which comprises administration of an effective amount of a compound of formula (I)

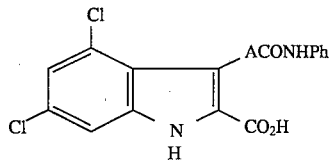

wherein A represents an unsubstituted ethenyl group in the trans (E) configuration, or a physiologically acceptable salt or metabolically labile ester thereof.

2. A method as claimed in claim 1 for the treatment or prevention of neurotoxic injury which follows cerebral stroke, thromboembolic stroke, hemorrhagic stroke, cerebral ischemia, cerebral vasospasm, hypoglycemia, anaesia, hypoxia, anoxia, perinatal asphyxia or cardiac arrest.

3. A method as claimed in claim 1 for the treatment or prevention of neurotoxic injury which follows cerebral stroke.

4. A method as claimed in claim 1 for the treatment or prevention of neurotoxic injury which follows cerebral ischemia.

5. A method as claimed in claim 1 for the treatment or prevention of neurotoxic injury which follows hemorrhagic stroke.

6. A method as claimed in claim 1 for the treatment or prevention of neurotoxic injury which follows thromboembolic stroke.

7. A method as claimed in claim 1 wherein the compound of formula (1) is administered in the form of the sodium salt thereof.

* * * * *